United States Patent [19]

Rose et al.

[11] Patent Number: 4,936,974
[45] Date of Patent: Jun. 26, 1990

[54] CAPILLARY SEPARATION SYSTEM WITH ELECTRIC FIELD ASSISTED POST SEPARATION MIXING

[75] Inventors: Donald J. Rose, Mountain View, Calif.; James W. Jorgenson, Chapel Hills, N.C.

[73] Assignee: The University of North Carolina at Chapel Hill, Chapel Hill, N.C.

[21] Appl. No.: 266,547

[22] Filed: Nov. 3, 1988

[51] Int. Cl.⁵ .................. G01N 27/28; G01N 27/26; B01D 57/02
[52] U.S. Cl. ............................. 204/299 R; 204/180.1
[58] Field of Search .............. 204/180.1, 299 R, 183.3

[56] References Cited

PUBLICATIONS

Van Vliet et al., "Post–Column Reaction Detection for Open–Tubular Liquid Chromatography Using Laser–Induced Fluorescence", Journal of Chromatography, 363 (1986) 187–198.
Scholten et al., "Fluorescence Detection of Chloroanilines in Liquid Chromatography Using Post–Column Reaction with Fluorescamine–Comparison of Reaction Types and Mixing Tees", Journal of Chromatography, 218 (1981) 3–13.
Lawrence et al., "Continuous Post–Column Ion–Pair Extraction Detection of Some Basic Organic Compounds in Normal–Phase Chromatography", Journal of Chromatography, 185 (1979) 473–481.
Tsuda & Kobayashi, "Post–Column Detection for Capillary Zone Electrophoresis", Journal of Chromatography, 456 (Dec. 1988) 375–381.
Pentoney, S. L. et al., "On–Line Connector for Microcolumns: Application to the On–Column o–Phthaldialdehyde Derivatization of Amino Acids Separated by Capillary Zone Electrophoresis", Analytical Chemistry, vol. 60, No. 23, (Dec. 1, 1988) pp. 2625–2629.
Weber, A. J. et al., "Peroxyoxalate Chemiluminescence Detection with Capillary Liquid Chromatography", Analytical Chemistry, vol. 59, No. 10 (1987) pp. 1452–1457.

Primary Examiner—John F. Niebling
Assistant Examiner—John S. Starsiak, Jr.

[57] ABSTRACT

A capillary zone electrophoresis (CZE) system provides for rapid, non-turbulent post-separation diffusional mixing of sample effluent with a fluorogenic-labelling reagent permitting sensitive detection of well-defined sample component zones. A separation capillary extends into a mixing capillary so as to define an annular gap therebetween. The effluent of the separation capillary is mixed with the labelling reagent, which is introduced through the annular gap. A power supply and opposing electrodes establish an electric field which induces electro-osmotic flow of the sample and charge-related differential electrophoretic migration to define component zones. The electric field also causes the separation capillary effluent to diverge as it issues into the mixing capillary so as to facilitate diffusional mixing with the reagent fluid flow without causing significant turbulence. Thus, fluorescence labelling is effective with minimum zone broadening. This system combines the high resolving power of CZE separation with the sensitivity of labelled fluorescence detection to attain an improved system for analyzing biological samples.

3 Claims, 7 Drawing Sheets

CAPILLARY SEPARATION SYSTEM WITH ELECTRIC FIELD ASSISTED POST SEPARATION MIXING

BACKGROUND OF THE INVENTION

The present invention relates to chemical analysis systems and, more particularly to an analytical instrument in which sample components are separated by differential electrokinetic migration through a narrowbore capillary. A major objective of the present invention is to provide for post-separation mixing of the sample with another fluid to aid in identification and quantification of the separated sample components. An illustrative example is the post-separation addition of a fluorogenic labelling reagent to separated protein components prior to fluorescence detection.

Chemical analyses of complex organic structures has made noteworthy advances in biotechnology possible. Biotechnology has provided techniques for manufacturing life-supporting medicines and other products which would otherwise be in short supply if natural sources had to be relied upon. In addition, entirely new medical products are in development which may arrest and cure heretofore untreatable diseases. Biotechnology promises new products for agriculture which will feed the world's expanding populations and which will enhance the ability of famine-prone countries to sustain themselves.

Chemical analysis of biological samples generally involves the separation of the samples into components for identification and quantification. Capillary zone electrophoresis (CZE) is one of a class of methods in which the different components are moved within a narrowbore capillary at respective and different rates so that the components are divided into distinct zones. The distinct zones can be investigated within the capillary or outside the capillary by allowing the components to emerge from the capillary for sequential detection.

In CZE, a sample is introduced at an input end of a longitudinally extending capillary and moved toward an output end. Electrodes of different potentials at either of the capillary generate the electrical forces which move the sample components toward the output end of the capillary. This movement includes two distinct components, one due to electro-osmotic flow and the other due to electrophoretic migration.

Electro-osmotic flow results from charge accumulation at the capillary surface due to preferential adsorption of anions from the electrolyte solution which fills the capillary bore. The negative charge of the anions attracts a thin layer of mobile positively charged electrolyte ions, which accumulate adjacent to the inner surface. The longitudinally extending electric field applied between the ends of the capillary by the electrodes attracts these positive ions so that they are moved toward the negative electrode at the output end of the capillary. These positive ions, hydrated by water, viscously drag other hydrated molecules not near this inner wall, even those with neutral or negative net charge. The result is a bulk flow of sample and the containing electrolyte solution toward the output end of the capillary. Thus, electro-osmotic flow provides a mechanism by which neutral and negatively charged, as well as positively charged, molecules can be moved toward a negative electrode. Typically, a CZE capillary has a bore diameter of less than 200 $\mu$m and preferable less than 100 $\mu$m, to ensure that the outer molecules interact sufficiently with more central molecules to effect an electro-osmotic flow which is fairly uniform across the capillary cross section.

Superimposed on this electro-osmotic flow is the well known motion of charged particles in response to an electrical field, commonly referred to as electrophoretic migration. The electrolyte solution acts as the medium which permits the electric field to extend through the capillary between the electrodes. Positively charged molecules migrate toward the negative electrode faster than the mean flow due to electro-osmotic flow. Negatively charged molecules are repelled by the negative electrode, but this repulsion is more than compensated by the electro-osmotic flow. Thus, negatively charged sample molecules also advance toward the negative electrode, albeit more slowly than the positively charged molecules. Neutral molecules move toward the negative electrode at an intermediate rate governed by the electro-osmotic flow.

After a sufficiently long migration through the separation capillary, the different sample components separate into bands or zones due to the differential movement rates as a function of species-specific charge. An appropriately selected and arranged detector can detect these zones seriatim as they pass. Components can be identified by the time of detection and can be quantified by the corresponding detection peak height and/or area. In some cases, the bands can be collected in separate containers for a distinct identification and/or quantification process.

There are several types of detectors used to detect proteins in capillary separation systems. Ultraviolet absorbance (UV) detectors are among the most common. Other electro-magnetic absorbance detectors could be used. In addition, chemi-luminescence, refractive index and conductivity detectors have been used. All these methods lack the sensitivity required to detect many peaks in CZE protein analysis. High sensitivity is required because the quantity of the total sample is limited, and the detector must be capable of detecting components that make up only of fraction of the total sample. Limitations on sample quantity stem from the requirement that the sample be dissolved in electrolyte and that the concentration of the sample be low enough to avoid perturbation of the electrical field which would lead to distortion of the separated component zones. The sample quantity is further limited by the capillary bore diameter and by the necessity of confining the sample initially to a relative short longitudinal extent. The initial sample extent governs the minimum zone breadth and thus the ability of the system to resolve similarly charged sample components.

The detector must be able to detect small quantities of the component in each sample zone. A UV detection system is faced with low concentrations and very short illumination path lengths and typically yields a poor signal-to-noise ratio. Other detection methods are similarly limited. Thus, while CZE is effective in separating protein components, there has been a limitation in finding a sufficiently sensitive detector for identifying and quantifying the separated components.

Fluorescence detection has been applied in conjunction with liquid chromatography (LC), a class of alternative component separation techniques. In liquid chromatography, a liquid "mobile" phase ushers components through a capillary at different rates related to the component's partitioning between the mobile phase and a stationary phase. Zones thus form as a function of partitioning ratios. The zones can be illuminated and the resulting fluorescence detected. Few proteins can be detected with sufficient sensitivity using their intrinsic fluorescence. However, labelling reagents can be used to enhance protein fluorescence. A major advantage of using fluorescence detection is that the increased sensitivity required by small sample quantities can be achieved by using very intense illumination. Thus, fluorescence detection used with labelling reagents promises to enhance the ability to identify and quantify sample components.

Unfortunately, liquid chromatography is not well suited for high resolution separation of proteins. While partitioning ratios differ among components, the molecules of any one component at any given time will be divided between the mobile phase and stationary phase, and thus move at different rates from each other. Despite averaging effects over the length of the capillary, sufficient zone broadening is induced by the partitioning to prevent high resolution separation of protein components. Since its only source of zone broadening is longitudinal diffusion, CZE represents an approximately ten-fold improvement in zone-breadth-limited resolution over liquid chromatography.

Fluorescence detection of proteins is not used in conjunction with CZE for a number of reasons. As in liquid chromatography, use of the fluorescence intrinsic to proteins in not generally applicable. Preseparation fluorescence labelling is incompatible with CZE for several reasons. For example, pre-separation labelling of protein components causes same-species molecules to have different charges. Thus, one component separates into multiple peaks, rendering detections virtually uninterpretable. Furthermore, sensitivity problems are aggravated because each peak represents only a fraction of a sample component.

Post-separation labelling involves the introduction of fluorogenic labelling reagent after separation and before detection. Post separation mixing is addressed by Van Vliet et al, "Post-Column Reaction Detection for Open-Tubular Liquid Chromatography Using Laser-Induced Fluorescence", *Journal of Chromatography*, Vol. 363, pp. 187-198, 1986. This article discloses the use of a Y-connector for introducing reagent into the effluent of a separation capillary. One problem with the Y-connector is the inevitable turbulence that occurs as the streams merge at an oblique angle. The turbulence stirs the sample stream, severely broadening the component zones. This broadening can be tolerable in a low resolution system, but not in a high-resolution CZE system.

Post-separation mixing is also addressed by Weber et al. in "Peroxyoxalate Chemilumininescence Detection with Capillary Liquid Chromatography" in *Analytical Chemistry*, Vol. 59, pp. 1452-1457, 1987. Weber et al. disclose the use of a Teflon tube to convey the separated sample components emerging from a liquid chromatography capillary, packed with silica particles to the interior of a mixing capillary. An annular gap between the Teflon tube and the mixing capillary is used to introduce chemi-luminescence reagent coaxially of the sample emerging from the narrower (0.2 mm) Teflon tube and into the (0.63 mm) mixing capillary. (Note that chemi-luminescence can not be employed in protein component detection.) Turbulence is minimized since the reagent flow is fast enough to define a sheathing flow confining the sample. However, a problem with the sheathing flow is that mixing occurs slowly. Sufficient mixing of the chemi-luminescence reagent with sample components thus requires a relatively long mixing interval and large mixing volume, during which zone broadening in the absence of impairs resolution significantly. While this zone broadening may be tolerable in the relatively low resolution liquid chromatography system disclosed, it would negate the advantages of a high resolution CZE system.

Thus, one obstacle to post-separation fluorescence labelling in high resolution systems is the attainment of rapid, yet low-turbulence and low volume, mixing of reagent and sample. However, CZE and other electrokinetic separation techniques face another obstacle to post-separation introduction of fluorescence labelling reagents, as well as other fluids. Fluid introduction generally requires apertures and other material inhomogeneities in capillary walls defining the sample path. In a CZE separation system, these inhomogeneities can cause field perturbations which interfere with electro-osmotic and other electro-kinetic effects. At a minimum these perturbations cause zone broadening, but can even partially or completely impair electro-kinetic movement of sample components.

In summary, CZE provides a separation technique which affords the resolution required for the analysis of complex proteins, but lacks a sufficiently sensitive compatible detection technique. Fluorescence detection provides a desirable level of sensitivity, but the required labelling has not been workable in the CZE context. What is needed is a system which combines the resolving power of CZE with the detection sensitivity of available with fluorescence-labelled proteins.

SUMMARY OF THE INVENTION

Basically, the present invention provides a system which permits post-separation introduction of a mixing fluid in a sample stream. The geometry and dimensions of the junction permitting this introduction are selected so that electro-kinetic effects are minimally impaired. In fact, the electric field can be used synergistically to facilitate diffusional mixing of sample and mixing fluid, keeping zone broadening to a minimum. Thus, the present invention provides for an effective combination of the resolving power of CZE separation with the detection sensitivity of fluorescence detection.

Preferably, the effluent end of a electrokinetic separation capillary is inserted into a mixing capillary, defining a region of overlap. An annular gap between the outer surface of the separation capillary and the inner surface of the mixing capillary serves as a port for introducing a fluorogenic-labelling reagent or other detection fluid. Electrodes are arranged relative to the separation capillary and mixing capillary so that an electric field extends from a positive electrode, through the bore of the separation capillary, radially across the annular gap, and through the bore of the mixing capillary to a negative electrode. The annular gap has a sufficiently small radial extent that the electric field is not substantially impaired by the gap. Thus, charged molecules of the separation capillary effluent are guided along the electric field across the annular gap and across the flow of the mixing fluid. Thus, the electric field acts to facilitate diffusional mixing of the effluent and mixing fluid. Therefore, the mixing is rapid and minimally turbulent, enhancing detection without significant zone broadening.

The Einstein equation for diffusion, $\bar{x} = (2Dt)^{\frac{1}{2}}$, establishes practical limits on the diameters of the separation and mixing capillaries required for sufficiently rapid diffusional mixing. The inner diameter of the mixing section of the mixing capillary should not exceed 200 μm and the maximum inner diameter of the separation capillary should not exceed 100 μm so that mixing times are limited to about a second. Preferably, the inner diameters are relatively similar. Of course, this requires a correspondingly thin wall for the separation capillary in the region of overlap. Such a thinned wall can be obtained by chemically etching a capillary to the desired extent.

In the application of primary interest herein, the mixing fluid is a fluorogenic-labelling reagent. The present invention allows this fluorogenic reagent to be mixed quickly with the sample effluent with minimal peak broadening. The small sample volume of a very low diameter separation capillary can be compensated by using intense radiation to stimulate fluorescence. Thus, the problem of the conflict between resolution and sensitivity is largely overcome. These and other features and advantages of the present invention are apparent from the description below with reference to the following drawings.

Figure 3:
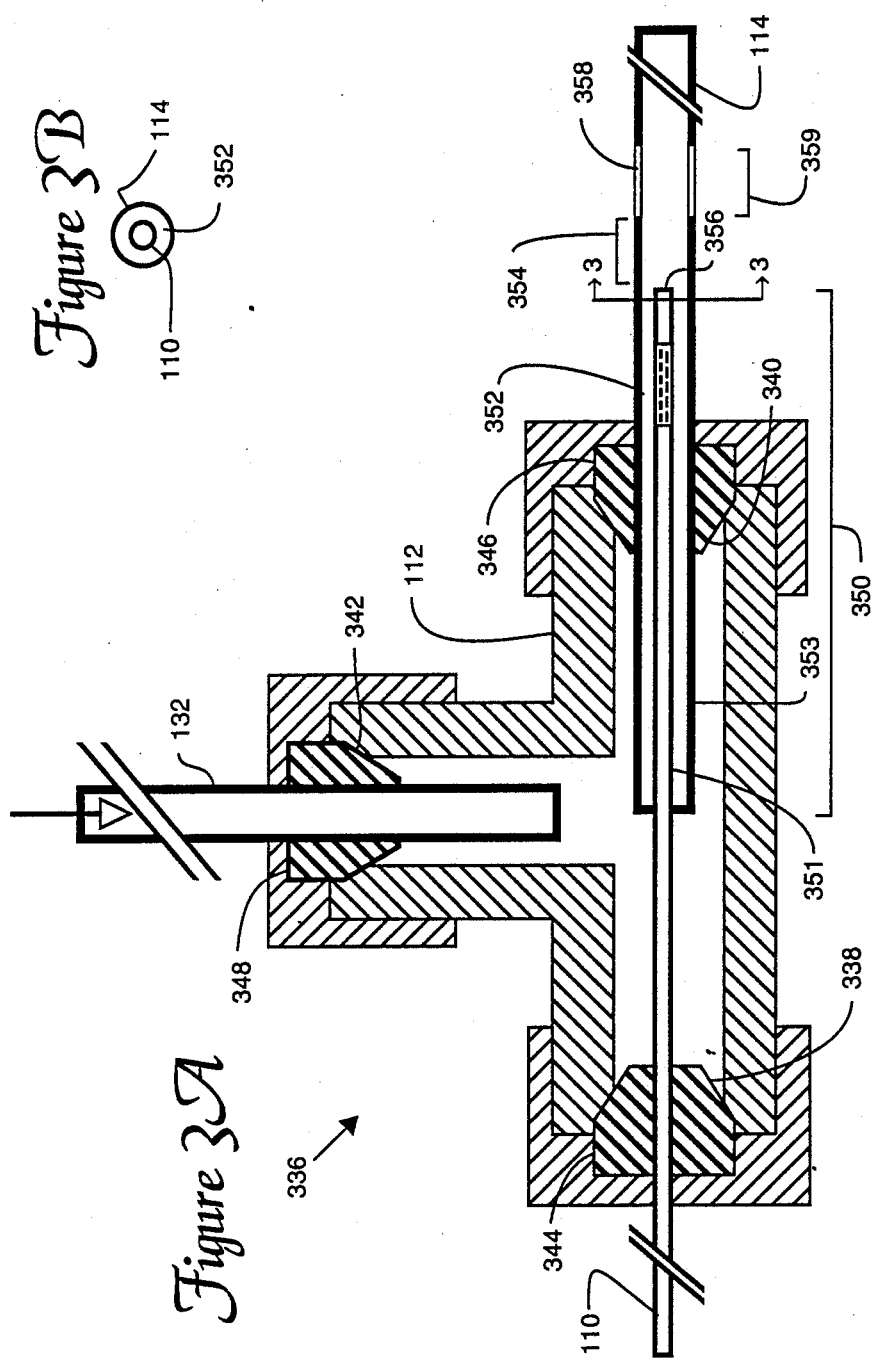
FIG. 3A is a schematic sectional view of a mixing junction of the system of FIG. 1.
FIG. 3B is a sectional view taken along line 3—3 of FIG. 3A.

In the figures, a three-digit number referring to an element of the drawings has as its first digit the figure number in which the element is introduced in the description below. For example, system 100 is first introduced with reference to FIG. 1 and junction 336 is first introduced with reference to FIG. 3. This is intended to aid the reader in locating a referent when it is now shown in the figure to which a given portion of the following description is explicitly referring.

DESCRIPTION OF THE PREFERRED EMBODIMENTS

A capillary zone electrophoresis (CZE) system 100 comprises high voltage supply 102, a first high voltage electrode 104, a first electrolyte reservoir 106 containing a solution of electrolyte 108, a separation capillary 110, a mixing tee 112, a mixing capillary 114, a fluorescence detector 116, a second electrolyte reservoir 118 also containing electrolyte 108, and a grounding electrode 120. Electrolyte 108, which also fills most of separation capillary 110 and mixing capillary 114, serves as a medium for the electric field between electrodes 104 and 120. The same electrolyte is used as a solvent carrier for the biological sample to be analyzed. A sample reservoir 122, with a second high voltage electrode 124 inserted therein, contains the sample solution 126. A reagent reservoir 128 contains reagent 130 which is directed along a reagent capillary 132 to mixing tee 112 for mixing with the effluent of separation capillary 110 within mixing capillary 114. Reagent flow is controlled by a pressure applied to reagent reservoir 128.

Sample solution 126 can be introduced into separation capillary 110 by inserting its input end 134 into sample solution 126. Voltage supply 102 is activated to establish an electric field from high voltage electrode 124, through separation and mixing capillaries 110 and 114, to grounding electrode 120. As electrolyte is drawn toward grounding electrode 120 by electro-osmotic flow, sample solution 126 is drawn into separation capillary 110 at its input end 134. Voltage supply 102 is turned off at the end of time interval required to introduce the appropriate amount of sample solution 126, which can be about 2 nanoliters.

Figure 1:
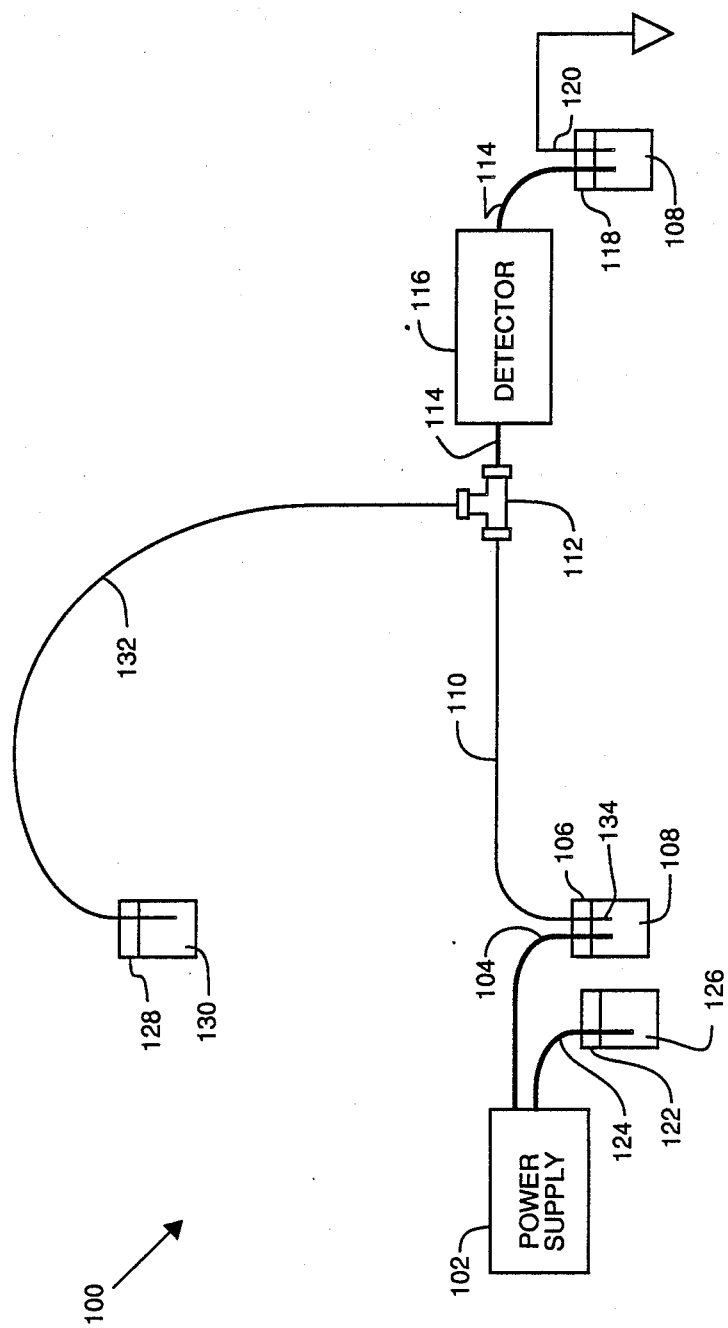
FIG. 1 is a schematic view of a capillary zone electrophoresis system in accordance with the present invention.

Input end 134 of separation capillary 110 is then inserted into the first electrolyte reservoir 108, to establish the configuration illustrated in FIG. 1. With voltage supply 102 again activated, the established electric field induces an electro-osmotic flow. Superimposed on this flow are relative electrophoretic migration rates which depend on the magnitude and sign of molecular charges. The result is that each sample component moves at a characteristic rate through separation capillary 110. The differential movement rates cause the sample components to exit separation capillary 110 into mixing capillary 114 and pass by fluorescence detector 116 at successive times.

Fluorescence detector 116 illuminates labelled sample components within mixing capillary 114 using a well-focused, high-intensity ultraviolet light, such as a mercury xenon arc lamp or a laser. Detector 116 includes a photo-multiplier tube which converts the resulting fluorescence intensity into a photo-current which is used to obtain an intensity vs. time output such as that shown in FIG. 2. The peaks correspond to different sample components, e.g., whale skeletal muscle myoglobin (WSM), carbonic anhydrase (CAH), β-lactoglobulin B (BLB) and β-lactoglobulin A (BLA). Specifically, the conditions were: 0.01% (weight/volume) WSM and CAH, 0.005% (weight/volume) BLA and BLB; operating and reagent electrolyte buffer 0.05M borate-0.05M KCl pH 9.5; 5 mg o-phthaldialdehyde (OPA) +50 μL mercaptoethanol+100 μL ethanol diluted to 4 mL with electrolyte buffer; sample introduction 2 s at 30 kV; run voltage 30 kV.

The resolution required to resolve the WSM and CAH peaks and the BLA and BLB peaks is obtained in part by using a small bore separation capillary. A bore diameter of 100 μm or less permits the electro-osmotic flow to act uniformly throughout the capillary cross section and prevents convection-induced zone broadening. Diameters smaller than 100 μm can be preferred to provide greater electrical resistance between electrodes 104 and 120. The greater resistance permits greater voltage for a given current. It is necessary to limit current to avoid boiling of the electrolyte. The higher voltage induces more rapid migration. More rapid migration results in less zone broadening due to diffusion (which is time-related) without compromising peak separation.

Figure 2:
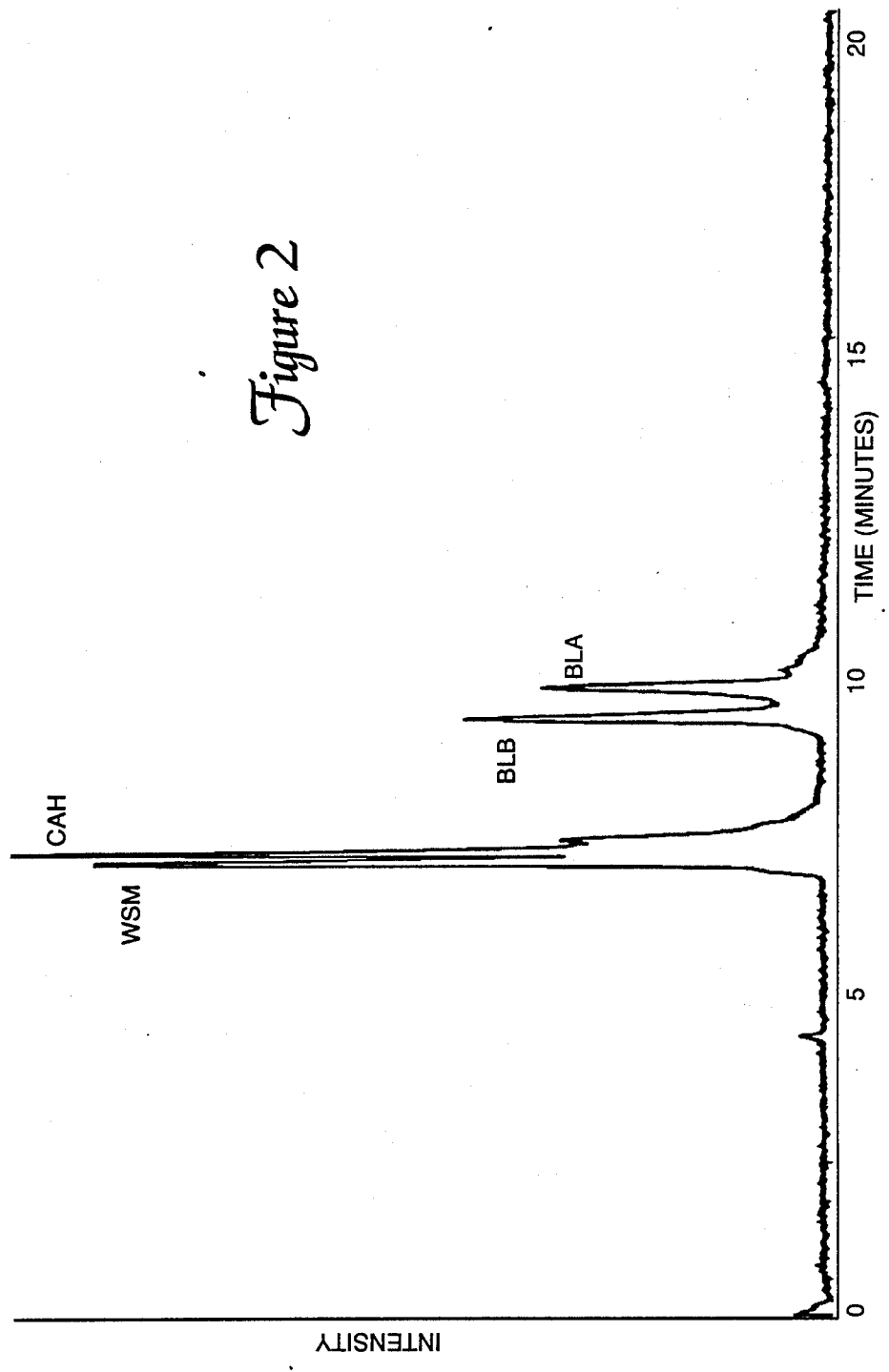
FIG. 2 is a graph showing the detector output for a sample.

The small sample volume available using small bore separation capillary 110 allows relatively little material to be available for detection. In the illustrated case, the sample proteins are diluted in electrolyte solution, and each peak of FIG. 2 represents only a fraction of the protein content of the sample. When UV absorption was used as the detection method for the same sample, the component peaks could not be distinguished clearly from other peaks due to noise. A similar problem would apply if the fluorescence detector had to rely on intrinsic fluorescence of the proteins. As indicated above, fluorescence labelling of a sample before separation is not a viable alternative. Consequently, the present invention provides a novel junction for permitting post-separation fluorogenic labelling. This is done in such a way as to minimize zone broadening while permitting a sufficiently strong component peak signal for identification and quantification of sample components.

Post-separation labelling is performed using the junction 336 illustrated in FIG. 3A. Stainless steel mixing tee 112 has two in-line ports 338 and 340 and an orthogonal port 342. Separation capillary 110 is supported by a first ferrule 344 where it extends through one in-line port 338, while the mixing capillary 114 is supported by second ferrule 346, where it extends through second in-line port 340. Reagent capillary 132 enters the short orthogonal port 342 where it is secured by a third ferrule 348. Fused silica reagent capillary 132 has an inner diameter of 200 μm, an outer diameter of 325 μm, and a length of 70 cm. Taking the direction of sample flow to define a longitudinal direction, then, in accordance with the present invention, separation capillary 110 extends into mixing capillary 114 so that the two are longitudinally overlapping, defining overlap region 350, and preferably concentric. Overlap region 350 includes an output section 351 of separation capillary 110 and an input section 353 of mixing capillary 114.

In overlap region 350 is defined an intermediate annular gap 352, illustrated in FIG. 3B, which provides fluid communication between mixing capillary 114 and a mixing section 354, shown in FIG. 3A, within mixing capillary 114 near the effluent end 356 of separation capillary 110. This permits the fluorogenic reagent 130 to mix with separation capillary effluent after sample component separation. After sufficient mixing, detection, i.e. sample illumination and fluorescence detection, can occur through a detection window 358 downstream of the mixing section 354.

Figure 4:
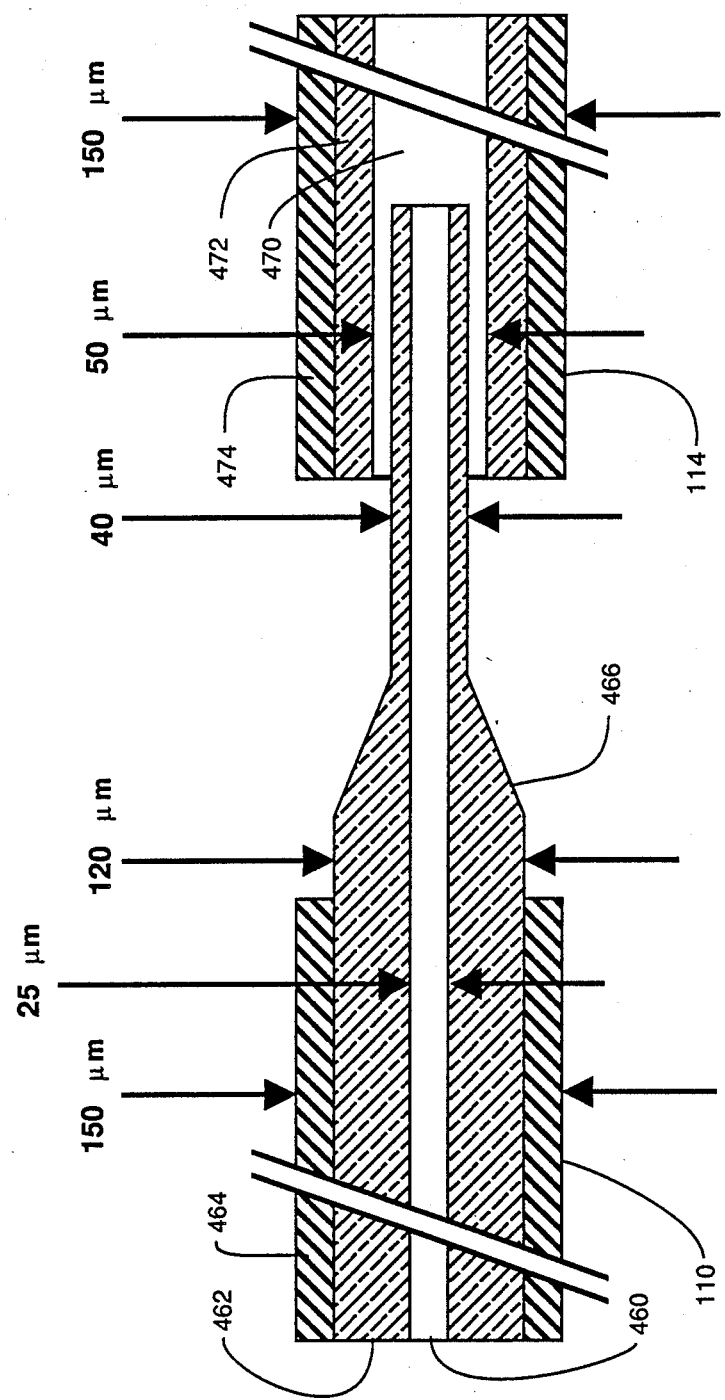
FIG. 4 is a sectional view of overlapping ends of a separation capillary and a mixing capillary in accordance with the present invention.

The preferred embodiment is shown in greater detail in FIG. 4. The separation capillary includes a central electrophoretic capillary bore 460, 25 μm in diameter, a fused silica wall 462, extending radially from the 25 μm diameter to 120 μm diameter. Separation capillary wall 462 is coated with a protective polyimide plastic coating 464, which has been removed near an exposed section 466 of separation capillary 110. Within exposed section 466, fused silica wall 462 is tapered to an outer diameter of 40 μm, which is the constant diameter of separation capillary output section 351. The inner diameter of the mixing capillary is then 50 μm.

Separation capillary 110 was formed by modifying a commercially available capillary tube having the dimensions of sepration capillary 110 as shown in FIG. 4 where plastic coating 464 is in place. The modification begins by stripping the coating over what will become exposed section 466 and then etching output end 468 in a stirred bath of concentrated (48%) hydrofluoric acid. During etching, water flows through separation capillary 110 toward the etchant solution to prevent interior etching.

Mixing capillary 114 has a bore 470 with inner diameter of 50 μm. A wall 472 defining bore 470 of the silica mixing capillary 114 has an outer diameter of 120 μm. It is important that the walls of separation and mixing capillaries 110 and 114 be of similar materials to enhance the continuity of the surface charge and thus electro-kinetic effects across intermediate annular gap 352; actually, fused silica is used for all three capillaries 110, 114 and 132, due to its flexibility, transparency, electrical insulation. A polyimide plastic coating 474 extends the outer diameter to 150 μm. Detection window 358 can be formed by burning off a 1–2 cm section of polyimide coating 474.

Figure 5:
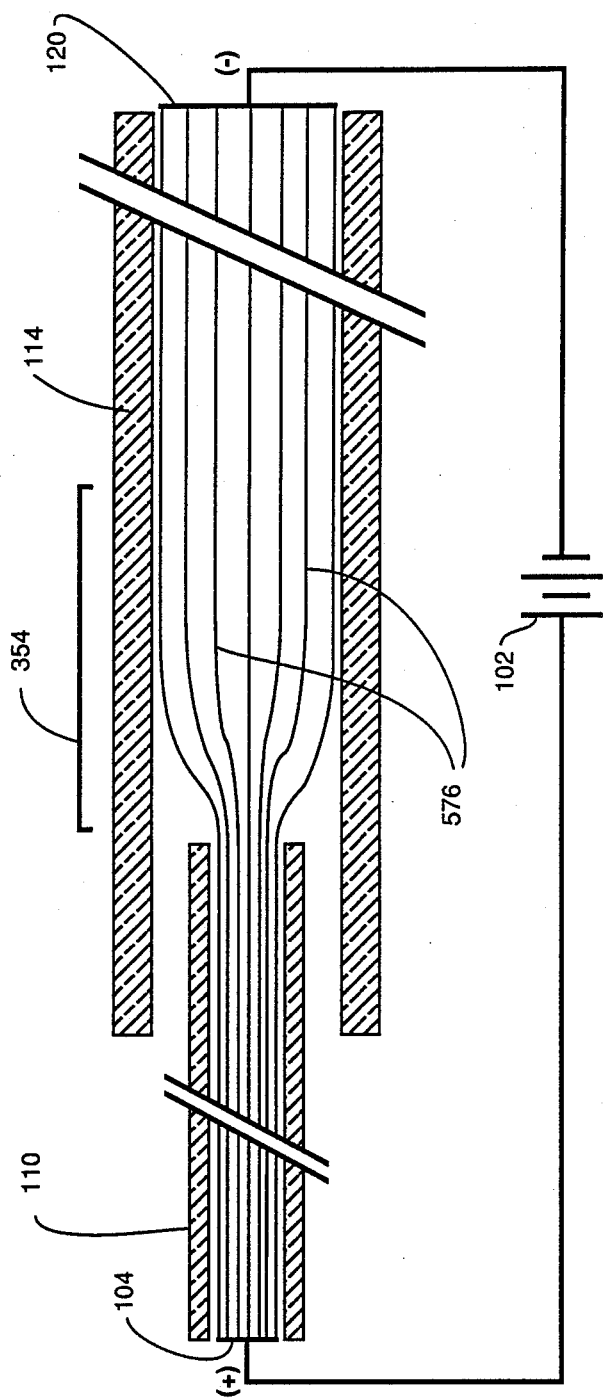
FIG. 5 is a view similar to that of FIG. 3 showing electric field perpendiculars.
Figure 6:
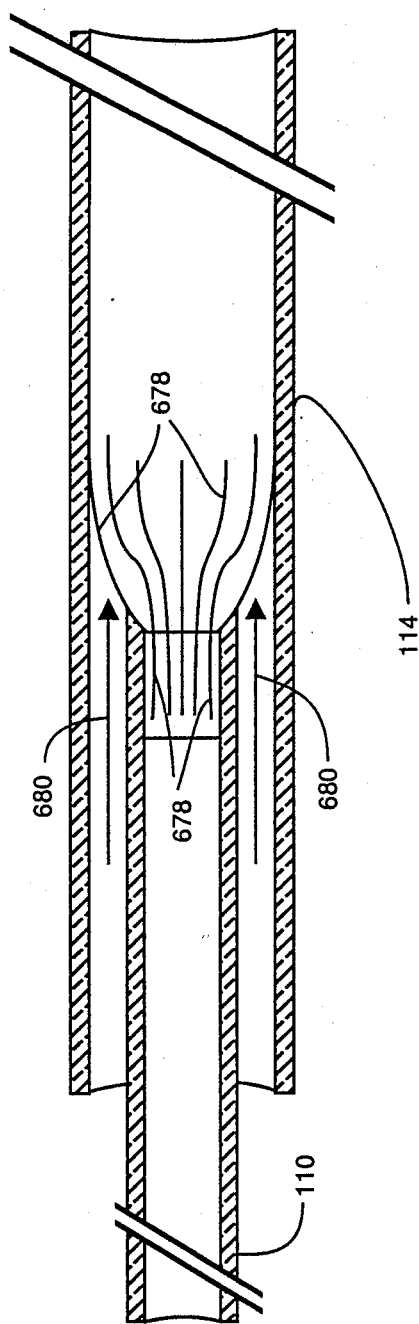
FIG. 6 is a view similar to that of FIG. 5 showing flow patterns.

Serendipitously, the electric field in overlap region 350 causes sample components to diverge radially across the trajectory for the reagent fluid flow. The electric field between high voltage electrode 104 and grounding electrode 120, shown in FIG. 1, establishes an electrical field 576, FIG. 5, through separation capillary bore 460 and mixing capillary bore 470, effectively defining a path for sample molecules. Electric field diverges radially at mixing section 354 and so guides separation capillary effluent 678 radially outward across the reagent flow 680 and toward the inner surface of the mixing capillary, as indicated in FIG. 6. Diverging effluent 678 facilitates diffusional mixing without undue turbulence. Electric field 576 thus assists diffusional mixing without significantly broadening component peaks. Accordingly, system 100 is well-suited for high-resolution protein analysis.

Use of coaxial junction 336 affords mixing of the o-phthaldialdehyde (OPA) reagent with migrating sample component zones without excessive zone broadening. Detector 116 is linear over three orders of magnitude and shows detection limits for amino acids and proteins in the femtogram (attomole) range. Other details relating to separation system 100 are described in "Instrumentation, Detection and Surface Deactivation in Capillary Zone Electrophoresis", by Donald J. Rose, Jr., a Ph.D. dissertation submitted to The University of North Carolina at Chapel Hill, (March, 1988), which dissertation is incorporated herein by reference.

Figure 7A:
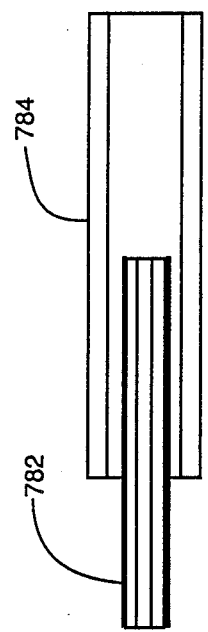
FIGS. 7A-7D are sectional views of overlapping ends of a separation capillary and a mixing capillary in accordance with the present invention.
Figure 7B:
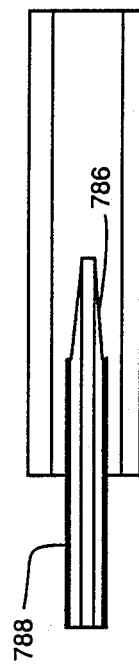
Figure 7C:
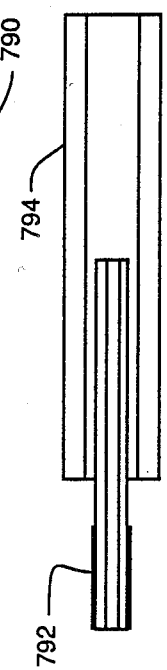

Several alternative junction types are provided for by the present invention. Two commercially available capillaries can be used with complementary dimensions to form the inventive junction, as shown in FIG. 7A. For example, a separation capillary 782 can have a constant inner diameter of 25 μm, a constant outer diameter of 150 μm, while the mixing capillary 784 has an inner diameter of 200 μm. In an alternative embodiment, the effluent end 786 of a separation capillary 788 is tapered to fit within a mixing capillary 790, as shown in FIG. 7B, rather than of constant outer diameter. Experimental results indicate that electrical field continuity is enhanced and turbulence is further minimized by decreasing the difference between the two inner diameters. By removing an outer coating from a section of a separation capillary 792, as indicated in FIG. 7C, so that its outer diameter is 110 μm in the region of overlap, one can use a mixing capillary 794 with a smaller inner diameter, for example, 160 μm.

Figure 7D:

The preferred embodiment, which is presented again for comparison in FIG. 7D, provided the most rapid and effective mixing. It is noted that the preferred embodiment had the minimum difference between inner diameters and thus the minimum average radial distance of effluent dispersion. In addition, the reagent and sample flow rates were most closely matched in the preferred embodiment.

The present invention also provides for other mixing section configurations. For example, mixing fluid can be introduced in a gap between two capillaries of similar inner diameters, the opposing ends of the capillaries being adjacent rather than overlapping. Alternatively, a single capillary can be used to provide both separation and mixing sections by forming an aperture in the wall of the capillary; mixing fluid can then be introduced into the sample stream through the aperture.

Choice of labels is limited by constraints of compatibility with separation process. Most fluorogenic labels are themselves fluorescent and thus add one or more peaks to detector output. To avoid the spurious fluorescence, the reagent must be completely reacted or excess reagent must be removed before detection. Both these alternatives are highly problematic. It is preferable to use fluorogenic labelling reagents which, like OPA, are not themselves fluorescent until they react with primary amine functions of protein molecules.

Generally, the present invention works best when the inner diameter of the separation capillary is less than 100 $\mu$m and the inner diameter of the mixing capillary is less than 200 $\mu$m. In addition, the cross-sectional area of the annular gap should be between 1 and 4 times that of the separation capillary. In the illustrated embodiment, the cross sectional area of the separation capillary is about 500 $\mu$m$^2$ and the cross sectional area of the intermediate annular gap is about 700 $\mu$m$^2$, for a ratio of about 1.4.

There are altenative electrokinetic separation techniques to CZE. Capillary polyacrylamide gel electrophoresis uses electrophoretic migration through a gel matrix. Capillary isoelectric focussing distributes sample components by isoelectric point in a pH gradient formed over the length of a capillary. Isotachophoresis distributes sample components by mobility. Micellar electrokinetic capillary chromatography is a form of chromatography which uses a "stationary" phase which is subject to electro-osmotic flow. All of these separation techniques require an electric field to cause movement and separation along capillaries. Accordingly, the present invention readily provides for the post-separation addition of a detection fluid in conjunction with the methods. The present invention can be applied to other capillary separation techniques by implementing an electric field to facilitate mixing, even though the electric field is not required for separation.

In the preferred embodiment, a fluorogenic labelling reagent is added after separation to enhance detection. The present invention accommodates other detection methods and thus the introduction of detection fluids adapted for these detection methods. For example, mass spectrometry can be used to analyze separated components. The present invention can be used to introduce a detection fluid, specifically, a carrier fluid, to sweep separated components into a mass spectrometer. These and other variations upon and modifications to the described embodiments are provided for by the present invention, the scope of which is limited only by the following claims.

What is claimed is:

1. A system comprising:
    sample path means defining a longitudinally extending sample path, said sample path means including a capillary separation section, a capillary mixing section, and a detection section arranged serially along said sample path, said separation section having a sample input end;
    sample introduction means for introducing a sample having plural components into said separation section at said sample input end;
    detection means for detecting the presence of any one of said sample components within said detection section provided said one of said sample components is sufficiently mixed with a predetermined detection fluid;
    electric field means for moving said sample components within said separation section toward said mixing section, through said mixing section and subsequently into said detection section, said electric field means including electrode means for applying an electric field along said sample path; and
    fluid introduction means for introducing said detection fluid into said mixing section so that said detection fluid mixes with said sample components so that said detection fluid and said sample components are sufficiently mixed before they move into said detection section so that said detection means can detect the presence of any one of said sample components.

2. The system of claim 1 wherein said mixing section includes an inner surface means, said electric field being characterized by electric field lines including electric field lines adjacent to said inner surface means, said detection fluid introduction means imposing a surface charge discontinuity in said inner surface means, said discontinuity having a maximum extent along said sample path of at most about 100 $\mu$m.

3. A protein analysis system comprising:
    a separation capillary, said separation capillary including an input end and an output section with an output end, said separation capillary having a nominal bore diameter of at most 100 $\mu$m, said output section having an outer diameter of at most 150 $\mu$m;
    sample input means for introducing a sample into said separation capillary at said input end, said sample including plural sample components, each component including molecules of a respective species;
    a mixing capillary having an upstream end, an overlapping section, a mixing section, and a detection section, said mixing capillary having a nominal bore diameter at most 200 $\mu$m and greater than said outer diameter of said output section of said separation capillary, said overlapping section being axially coextensive with said output section of said separation capillary so that the effluent of said separation capillary issues into said mixing section and so that an annular gap is defined between said output section and said overlapping section, said separation capillary and said mixing capillary jointly defining a sample path;
    fluorogenic labelling fluid introduction means for introducing a fluorogenic-labelling fluid into said mixing section through said annular gap;
    fluorescence detection means for detecting protein molecules labelled with said fluorescence-labelling fluid; and
    electric means for establishing an electric field along said sample path so as to induce said sample to move from said input end along said sample path, through said mixing section and into said detection section, said electric field causing said plural components to move at different respective rates through said separation capillary so that they issue from said output end at different times, said electric field causing at least some of said molecules to move radially outward after issuing from said output end so as to effect rapid non-turbulent diffusional mixing with said fluorescence labelling fluid.

* * * * *